Figure 3:
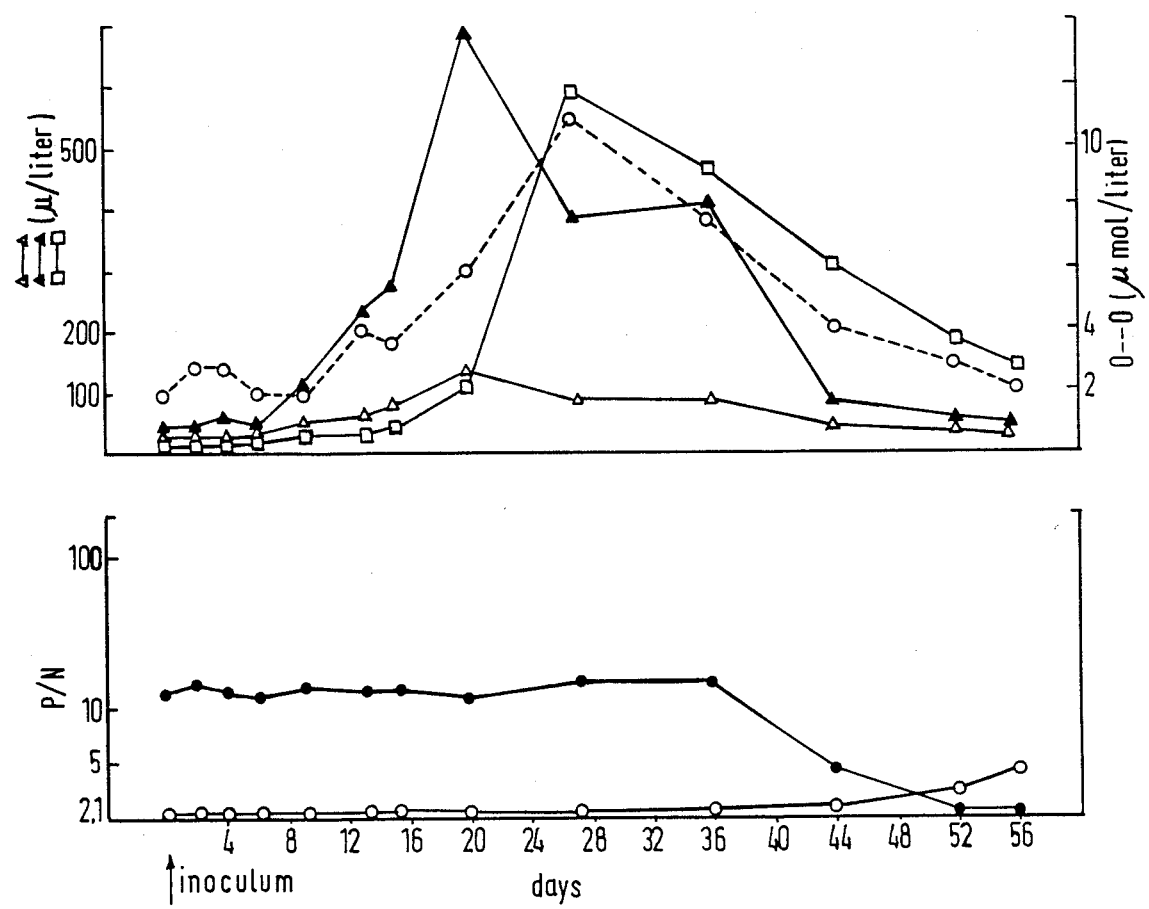

United States Patent [19]

Dijkema et al.

[11] Patent Number: 4,959,462
[45] Date of Patent: Sep. 25, 1990

[54] DESOXYRIBONUCLEIC ACID; MICROORGANISMS; DIAGNOSTIC AGENT FOR DELTA INFECTION AND THE USE THEREOF

[75] Inventors: Reinder Dijkema, Oss; Antonides Kos, Leiden, both of Netherlands

[73] Assignee: Nederlandse Centrale Organisatie voor Toegepast-Natuurwetenschappelijk Onderzoek, The Hague, Netherlands

[21] Appl. No.: 823,196

[22] Filed: Jan. 28, 1986

[30] Foreign Application Priority Data

Jul. 31, 1984 [NL] Netherlands .................. 8402392

[51] Int. Cl.$^5$ .................. C07H 21/04; C12Q 1/68; C12N 15/00; G01N 33/53
[52] U.S. Cl. .................. 536/27; 435/6; 435/7; 435/172.3; 435/320; 436/501; 436/811; 436/813; 935/3; 935/29; 935/56; 935/78
[58] Field of Search .................. 536/27; 435/320, 6, 435/7, 172.3; 436/501, 811, 813; 935/3, 29, 56, 78

[56] References Cited

U.S. PATENT DOCUMENTS 4,619,896 10/1986 Shattock et al. .................. 435/7
4,711,955 12/1987 Ward et al. .................. 536/29

FOREIGN PATENT DOCUMENTS 0131974 1/1985 European Pat. Off. .
0174669 3/1986 European Pat. Off. ............ 435/320

OTHER PUBLICATIONS

Tiollais, P. et al. (1985), Nature, 317, pp. 489–495.
Richman, D. D. et al. (1984), J. of Infectious Diseases, 149(3), pp. 298–310.
Chemical Abstracts, vol. 100, No. 21, 21st May 1984, p. 328, col. 1, Abstract No. 171214k, Columbus, Ohio, U.S.; B. Hoyer et al.: "Properties of Delta-Associated Ribonucleic Acid"; & Prog. Clin. Biot. Res., vol. 143, 1983, pp. 92–97.
Chemical Abstracts, vol. 104, No. 21, 26th May 1986, p. 326, cols. 1, 2, Abstract No. 182922y, Columbus, Ohio, U.S., Ne. Cen. Org. voor Toegepast-Natuurwetenschappelijk Onderzoek; "Deoxyribonucleic Acid, Microorganisms, Diagnositc Means for Delta Infection, and Use There Of"; N.A. 8402392 published 17th Feb. 1986, priority 31st Jul. 1984.
Chemical Abstracts, vol. 105, No. 1, 7th Jul. 1986, p. 149, col. 2, Abstract No. 1518y, Columbus, Ohio, U.S.: K. J. Denniston et al.: "Cloned Fragment of the Hepatitis Delta Virus RNA Genome: Sequence and Diagnostic Application"; & Science vol. 232, 1986, pp. 873–875.
Chemical Abstracts, vol. 100, No. 17, 23rd Apr. 1984, p. 481, col. 2, Abstract No. 137082f, Columbus, Ohio, U.S.; F. Bonino et al.: "Delta Hepatitis Agent: Structural and Antigenic Properties of the Delta Associated Particle"; & Infect. Immun., vol. 43, No. 3, 1984, pp. 1000–1005.
Wang et al, Nature, 323, 508–514 (1986).
Denniston et al, The Chemical Abstracts 105:1518y (1986).

Primary Examiner—Amelia B. Yarbrough
Assistant Examiner—Ardin Marschel

[57] ABSTRACT

This invention relates to DNA having at least 60% homology relative to γ-RNA or a portion thereof and the capacity of selective hybridization with δ-RNA. Such DNA, if provided with a detectable label, such as $^{32}$P can be used as a diagnostic agent to diagnose δ infection.

9 Claims, 3 Drawing Sheets

```
              10         20         30         40         50         60
5'→ CCCCGTTGCT TTCTTTACTT TCCTCCTCGC TTCGGTCTCC CCCTACTCCT AGCATCTCCT
    GGGGCAACGA AAGAAATGAA AGGAGGAGCG AAGCCAGAGG GGGATGAGGA TCGTAGAGGA 70         80         90        100        110        120
    CCTATCGCTA TGGTCTTACT CCTACCGCTC GAAGCGCCTC TTGTTCGCTG AAGGGGTCCT
    GGATAGCGAT ACCAGAATGA GGATGGCGAG CTTCGCGGAG AACAAGCGAC TTCCCCAGGA 130        140        150        160        170        180
    CTGGAGGTGA TTTCTCTGCT CATCTCCGAG TGGATTCCTC CCTCTGGGTG CTACTCAACC
    GACCTCCACT AAAGAGACGA GTAGAGGCTC ACCTAAGGAG GGAGACCCAC GATGAGTTGG 190        200        210        220        230        240
    CTTCGGGCCG GAGTGCTCTC CAGATCTGGA GGTTGGGCCC CTCGGATCGG GAGGCCCGCT
    GAAGCCCGGC CTCACGAGAG GTCTAGACCT CCAACCCGGG GAGCCTAGCC CTCCGGGCGA 250        260        270        280        290        300
    CCTTTTTCTT CCACCTTCCT CTTTCCCCTT CCAGAGATTC TCCGGCGTTG TGGGGATCTC
    GGAAAAAGAA GGTGGAAGGA GAAAGGGGAA GGTCTCTAAG AGGCCGCAAC ACCCCTATAG 310        320        330        340        350        360
    GTCCGCTTCC TGAGACCTCT CTTTGCTTCT TGGGAGTAGT TTCTCCGACG TTCCAATGCT
    CAGGCGAAGG ACTCTGGAGA GAAACGAAGA ACCCTCATCA AAGAGGCTGC AAGGTTACGA 370        380        390
    CTTTACCGTG ACATCCCCTC TCGGGAGCTG A
    GAAATGGCAC TGTAGGGGAG AGCCCTCGAC T ←  5'
```

FIG. 1

```
              10         20         30         40         50         60
5'→   CCCGGTGCT TTCTTTACTT TCCTCCTCGC TTCGGTCTCC CCCTACTCCT AGCATCTCCT
      GGGCCAACGA AAGAAATGAA AGGAGGAGCG AAGCCAGAGG GGGATGAGGA TCGTAGAGGA 70         80         90        100        110        120
      CCTATCGCTA TGGTCTTACT CCTACCGCTC GAAGCGCCTC TTGTTCGCTG AAGGGGTCCT
      GGATAGCGAT ACCAGAATGA GGATGGCGAG CTTCGCGGAG AACAAGCGAC TTCCCCAGGA 130        140        150        160        170        180
      CTGGAGGTGA TTTCTCTGCT CATCTCCGAG TGGATTCCTC CCTCTGGGTG CTACTCAACC
      GACCTCCACT AAAGAGACGA GTAGAGGCTC ACCTAAGGAG GGAGACCCAC GATGAGTTGG 190        200        210        220        230        240
      CTTCGGGCCG GAGTGCTCTC CAGATCTGGA GGTTGGGCCC CTCGGATCGG GAGGCCCGCT
      GAAGCCCGGC CTCACGAGAG GTCTAGACCT CCAACCCGGG GAGCCTAGCC CTCCGGGCGA 250        260        270        280        290        300
      CCTTTTTCTT CCACCTTCCT CTTTCCCCTT CCAGAGATTC TCCGGCGTTG TGGGGATCTC
      GGAAAAAGAA GGTGGAAGGA GAAAGGGGAA GGTCTCTAAG AGGCCGCAAC ACCCCTATAG 310        320        330        340        350        360
      GTCCGCTTCC TGAGACCTCT CTTTGCTTCT TGGGAGTAGT TTCTCCGACG TTCCAATGCT
      CAGGCGAAGG ACTCTGGAGA GAAACGAAGA ACCCTCATCA AAGAGGCTGC AAGGTTACGA 370        380        390
      CTTTACCGTG ACATCCCCTC TCGGGAGCTG A
      GAAATGGCAC TGTAGGGGAG AGCCCTCGAC T ←5'
```

FIG. 2

```
Pro Leu Leu Ser Leu Leu Ser Ser Leu Arg Ser Pro Pro Thr Pro Ser Ile
CCG TTG CTT TTA CTT TCC TCG CTT CGG TCT CCC CCT ACT CCT AGC ATC

Ser Tyr Arg Tyr Gly Leu Thr Pro Thr Ala Arg                 Ser Ala Ser Cys Ser Leu
TCC TAT CGC TAT GGT CTT ACT CCT ACC GCT  CGA                AGC GCC TCT TGT TCG CTG
                                         TaqI

Lys Gly Ser Gly Gly Asp Phe Ser Ala His Leu Arg Val Asp Ser Ser Leu
AAG GGG TCT GGA GGT GAT TTC TCT GCT CAT CTC CGA GTG GAT TCC TCC CTC

Trp Val Leu Leu Asn Pro Ser Gly Arg Ser Ala Leu Gln Ile Trp Arg Leu Gly
TGG GTG CTA CTC AAC CCT TCG GGC CGG AGT GCT CTC CAG ATC TGG AGG TTG GGC
                                                      BglII

Pro Ser Asp Arg Glu Ala Arg Ser Phe Phe Phe His Ley Pro Leu Ser Pro Ser
CCC TCG GAT CGG GAG GCC CGC TCC TTT TTC CAC CTT CCT CTT TCC CCT TCC

Arg Asp Ser Pro Ala Leu Trp Gly Ser Arg Pro Leu Pro Glu Thr Ser Leu Cys
AGA GAT TCT CCG GCG TTG TGG GGA TCT CGT CCG CTT CCT GAG ACC TCT CTT TGC

Phe Leu Gly Val Val Ser Pro Thr Phe Gln Cys Ser Leu Pro  ***  His Pro Leu → AvaI
TTC TTG GGA GTA GTT TCT CCG ACG TTC CAA TGC TCT TTA CCG  TGA  CAT CCC CTC
```

DESOXYRIBONUCLEIC ACID; MICROORGANISMS; DIAGNOSTIC AGENT FOR DELTA INFECTION AND THE USE THEREOF

The delta (δ) agent is a transmissible human pathogen that superinfects individuals having type B viral hepatitis in either the acute phase or the chronic carrier state. Since its discovery by Rizetto et al, Gut 18,997-1003 (1977) no certainty as to its identity has been obtained.

The hypothesis that the δ agent is a variant of the hepatitis B virus (HBV) should apparently be rejected on the basis of extensive transmission studies in the chimpanzee of selected inocula which do contain transmissible HBV but give no δ infection. The hypothesis that the δ agent is a non-defective infectious virus differing from HBV must be rejected on the ground of the finding that δ infection requires the presence of HBV (HBSAG) surface antigen. Epidemiological data in humans and transmission studies in chimpanzees have established the helper function of HBV in δ infection. Using immuno fluorescence, the δ-antigen/antisystem has been detected and identified, revealing no immunologic relationship to the known antigen/antibody (AG-/AB) systems of HBV (i.e., surface(s), core(c) and envelope(e) antigen, respectively). In experimental infection in chimpanzees, however, the presence of δ-AG was found to be always associated with a discrete subpopulation of HBsAg particles. These particles measure 35 to 37 nm in size and are composed of the δ Ag and an associated low-molecular RNA encapsulated by HBsAg. Although the particles per se are not unique for δ infection, the presence of the -Ag-associated small RNA could only be observed in serum taken during the acute phase of infection, both in man and in the chimpanzee. The amount of RNA was found to be proportionate to the relative δ-Ag concentration in the serum, while a specific immuno precipitation with anti-HBsAg was found to be possible.

The supposed helper functions of HBV in δ infection (i.e., replication and encapsulation) and the small size of the RNA have led to the hypothesis that the agent is a unique defective agent, which, for its reproduction, needs one or more HBV helper functions (for replication and expression) and that the δ RNA with its subviral size only encodes the genetic information for the δ antigen. The suppression of circulating HBV markers (HBV/DNA) observed during the superinfection of HBV-infected chimpanzees with the δ agent suggests that the agent disturbs the replication of the helper HBV. The encapsulation of the δ agent with HBsAg may be a different HBV helper function owing to which the agent can approach susceptible hepatocytes.

Starting from this hypothesis it has been endeavoured, and successfully so, to provide, by means of recombinant DNA technology, applied to the δ-antigen associated RNA, a new diagnostic agent for δ antigenemia, i.e. the presence of δ antigen in, for example, blood, at the RNA/DNA level, which avoids the disadvantages of existing immunological analysis for δ-antigen i.e. the disturbance of the existing solid-phase radioimmunoanalysis owing to the presence of high antititers. The preparatory work comprised the isolation of the δ-Ag associated RNA from acute-phase serum of experimentally infected chimpanzees, molecular cloning and partial copy DNA (cDNA) sequence analysis. Structural analysis by means of electron microscopy and determining the size of the RNA by means of agarose gel electrophoresis (approx. $5 \times 10^5$ dalton) led to the conclusion that the δ-RNA is a linear single strand molecule which upon renaturation exhibits a strong degree of intramolecular base-pairing. By using this property it was possible to realize a molecular cloning of the δ-RNA, which was productive of a partial cDNA clone approx. onethird of the length of the total genome. By using this cDNA clone as a probe we were able to reject the hypothesis that the δ-Ag associated RNA is the product of a HBV variant, because no cross hybridization took place with southern and northern blots containing HBV DNA from the serum of a chimpanzee during HBsAg antigenemia. We were also able to reject the hypothesis that the δ-Ag associated RNA is a unique component of the host, which is artificially coated with δ-Ag and encapsulated by HBsAg, and this because no hybridization took place with either chromosomal DNA or total liver RNA of the same chimpanzee prior to HBsAg antigenemia. Nucleotide sequence analysis of the resulting partial cDNA, and hybridization experiments with δ-RNA and strand-specific DNA probes, when it was found that only the probe carrying the hypothetical open reading frame for protein biosynthesis showed hybridization, led to the ultimate conclusion that the δ agent is a negative strand virus in which an RNA complementary to the δ-RNA will encode δ-Ag.

Thus the present invention provides a probe that can be used for the clinical diagnosis of δ infection and is free from the disadvantages inherent in immunological analyses referred to hereinbefore.

For this purpose the invention provides a desoxyribonucleic acid (DNA) comprising DNA with at least 60% homology relative to a portion of δ-ribonucleic acid (δ-RNA) and the capacity of selective hybridization with δ-RNA.

In a specific embodiment the invention provides such a DNA which additionally comprises vector DNA. A suitable example is a plasmid composed of vector DNA and cDNA. The invention comprises micro-organisms, such as *Escherichia coli* containing such a DNA.

The invention further provides a diagnostic agent for diagnosing δ infection, comprising a DNA according to the invention provided with a detectable label. Such detectable labels are known per se. Highly suitable is the radial label $^{32}P$.

The invention finally comprises the use of a diagnostic agent according to the invention for diagnosing δ infection. In it, use is made in a manner known per se of the capacities of selective hybridization of the labelled probe according to the invention with δ—RNA.

The invention will be illustrated in and by the following experimental section. The accompanying FIG. 1 shows the base sequence of a portion of the partial δ-cDNA. FIG. 2 shows the codons and associated amino acids; FIG. 3 shows the immunological, serological and biochemical events in a given champanzee after inoculation with the δ agent.

Source of the antigen associated RNA

Susceptible chimpanzees (*Pan troglodytes*) were infected with hepatitis B virus and the infections were followed by means of serological markers for HBsAg anti HBsAg, alanine amino transferase (ALT), aspertate amino transferase (AST), bilirubin, δ-glutamate transpeptidase (GGTP). During the accute phase of H(V infection, as determined by the serological markers and HBV DNA the animals were superinfected by the intravenous administration of δ agent derived from the acute-phase serum of a chronic HBsAg-carrier chimpanzee showing intrahepatic and circulating δ-antigen.

Isolation of nucleic acids

Serial samples from chimpanzees infected with δ agent were analysed for the δ-antigen associated RNA by layering each serum sample onto a 4 ml. cushion of 20% (w/w) sucrose in 0.01 M phosphate pH 7.9/0.85% NaCl and ultracentrifugation at 200,000 xg at 4° C. for 5 hours in a Beckman SW 41 rotor as described by Rizetto et al., Proc.Natl.Acad.Sci. USA 77,6124–6128 (1980). particles were extracted for nucleic acid content by resuspension in 0.2 M NaCl/0.01 M sodium EDTA/2% Na Dod $SO_4$/0.05 M Tris-HCl, pH 8.0/1 mg/ml proteinase K (Sigma) and incubation for 1–2 hours at 37° C. After extraction with equal volumes of phenol and chloroform the aqueous phase was precipitated with ethanol. Further investigation comprised the use of electron microscopy and gel electrophoresis in which nucleic acids were analysed by 0.6–1.5% horizontal agarose gel electrophoresis under both native and denaturing conditions.

Molecular cloning of cDNA

Nucleic acids derived from acute-phase serum particles and precipitated with ethanol were used directly for cDNA synthesis by the procedure described by Ohno et al. in Nucl.Acids Res.11, 6185–6202 (1983), except that the samples were previously heated in water at 70° C. for 5 minutes and cooled in solid carbon dioxide-ethanol. By means of AMV reverse transcriptase, DNA complementary to the δ antigen associated RNA was then synthesized as described by Efstratiados et al. in Cell 7, 279–288 (1976), except that no exogenous primer was added. The single-stranded cDNA was used as a primer-template for the synthesis of the second strand by means of the Klenow fragment of DNA polymerase. This was followed by $S_1$ nuclease digestion, sizing of double-stranded cDNA, tailing of double-stranded cDNA/vector and transformation of competent E.coli as described by Dijkema et al. in Nucl.Acids Res. 12, 1227–1242 (1984).

Screening of recombinant clones

E.coli transformants containing sequences of the δ antigen associated RNA were screened by in situ colony hybridization according to Grunstein et al. Proc.Natl.Acad.Sci.USA 72, 3961–3965 (1975), using RNA derived from either acute phase serum particles or control liver as a probe. $^{32}$P-RNA fragments were prepared by partial hydrolysis of the RNA in 25 mM glycine-NaOH, pH 9.0, 5 mM $MgCl_2$ at 37° C. for 3 hours (see the above publication by Ohno et al.) and subsequent labelling with δ-$^{32}$P/ATP and $T_4$ polynucleotide kinase. After incubation at 37° C. for 30 minutes the labeled RNA fragments were extracted with phenol/chloroform and precipitated with ethanol. Hybridization in 50% formamide and washing were performed as described in the above publication by Dijkema et al.

Southern and Northern blotting

DNA/RNA samples were fractionated by electrophoresis under non-denaturing or denaturing (formaldehyde) conditions in 0.6–1.5% agarose gels. Fractionated samples were transferred to either Schleicher and Schull (BA 85) or Gene Screen nitrocellulose filters for non-denaturing and denaturing gels, respectively. Condition for hybridization and washing were in conformity with suppliers' specification.

DNA sequencing was performed as described by Maxam et al., Proc.Natl.Acad.Sci.USA 74, 560–564 (1977).

Results

Transmission of δ agent to susceptible chimpanzees.

FIG. 3 shows the immunological, serological and biochemical events occurring in one of the chimpanzees (no.15) after inoculation with the δ agent. The presence (+) or absence (−) of HBV DNA and δ-antigen associated RNA, as assayed by agarose gel electrophoresis is indicated at the top. The middle part of the figure shows in diagrammatic form the presence of the serological markers ALT (black triangles), AST (white triangles), bilirubin (white circles) and GGTP (white squares). The bottom part of the figure shows, in diagrammatic form, the titer of the serum HBsAg (black circles) and the anti-HBsAg (white circles), expressed as the ratio of positive to negative (P/N).

At the time of superinfection with the δ agent, the animal exhibited antigenemia due to HBsAg, as shown by circulating HBsAg and HBV DNA. Superinfection resulted in a transient antigenemia, marked by elevated ALT-AST levels 3 weeks after inoculation. Although during this period the amount of circulating HBsAg remained virtually constant, the HBV DNA level had become markedly lower 2 weeks after inoculation. δ-antigen associated RNA was detected as early as 2 weeks after inoculation and reached an optimum after 3 weeks, which coincided with the ALT-AST markers. After 4 weeks no δ-antigen associated RNA could be detected any longer, and the animal sera converted to anti-HBsAg 7 weeks after inoculation.

Molecular cloning

Because the structural analysis (electron microscopy) of the RNA associated with δ-antigen revealed a single stranded linear nature, we first investigated the presence of a poly(A)tail. We were, however, unable to show the presence of a poly(A)tail either by binding the RNA to oligo (dT)cellulose columns or by priming the cDNA synthesis with oligo (dT) 12–18. Since, under native conditions, the RNA will form a structure with high internal base pairing it was assumed that the existing free 3'-end might serve as a primer for the synthesis of its own cDNA. The cDNA prepared in this manner was cloned by standard techniques and amplified by the propagation of hybrid vectors in E.coli. Recombinant clones were screened by differential hybridization with $^{32}$P-labelled RNA derived from either acute phase serum or control liver. One transformant only gave a positive reaction with the RNA probe from the acute phase serum. This clone, designated p δ-1 was subsequently used as a probe to screen a Northern blot of fractionated RNA samples isolated throughout the acute phase of antigenemia in chimpanzee no. 15. It was found that hybridization only occurred with samples previously shown to contain δ-antigen associated RNA, and the position of migration coincided with the estimated (single) stranded length of 1750 nucleotides. No hybridization was observed with total liver RNA, chromosomal DNA extracted prior to HBsAg antigenemia, or total serum DNA extracted during HBsAg antigenemia of chimpanzee no. 15, in Northern and Southern blots.

Nucleotide sequence of p δ-1

As we had used the technique of dG/dC tailing, applied to pBR322 and δ-cDNA cleaved with the restriction enzyme PstI, we were able to remove the inserted fragment again by incubation with PstI. The insert length of p δ-1 was estimated to be 520 base pairs. Its nucleotide sequence was partly determined and is shown in FIG. 1. The 3 possible frames have been investigated for the occurrence of translation termination codons (TAA, TGA and TAG). Only one frame showed a stretch of appreciable length before a stop codon (TGA) appeared 70 base pairs before the end of the cDNA. The translation product of part of this hypothetical gene is shown in FIG. 2.

Strand specificity of δ-antigen associated RNA

In order to identify which strand of p δ-1 was equivalent to the δ-antigen associated RNA to strand-specific DNA probes were made. For this purpose p δ-1 was digested with the restriction enzyme BglII (having only one cutting position in the δ-cDNA part of p δ-1) and the corresponding ends were labelled with γ-$^{32}$p ATP and T4 polynucleotide kinase. The labelled hybrid vector was then digested with either the restriction enzyme AvaI or the restriction enzyme TaqI, and the labelled fragments were separated on a 5% polyacrylamide gel, isolated, and used for hybridization with RNA samples isolated from the acute phase serum of chimpanzee no. 15. It was found that only the BglII-AvaI probe showed a positive hybridization with the δ-Ag associated RNA, which showed that its complementary strand was equivalent to the RNA.

On Jan. 6, 1986 a strain of E.coli JA 221 (p δ-1), containing the plasmid p δ-1, was deposited with the Centraal Bureau voor Schimmelcultures (CBS) at Baarn, the Netherlands, under no. CBS 101.86.

Practical application 1-2 ml of the serum of 6 patients, whom we did not know to have a δ agent infection, was processed for an RNA isolation according to the procedure described above under 'Isolation of nucleic acids'. After hybridization of the radio-activated δ sequence with the RNA preparations, it was shown that in 3 of the 6 patients particles were present in the serum. This result corresponded to the results obtained by using an immunological analysis for the presence of δ antigen.

I claim:

1. The DNA having at least 60% homology relative to a portion of δ-RNA and being capable of selective hybridization with δ-RNA.

2. The DNA as claimed in claim 1, comprising copy DNA of a portion of the δ-RNA, said copy DNA being capable of selective hybridization with δ-RNA.

3. A diagnostic agent for diagnosing δ infection, comprising DNA as claimed in any one of claims 1 and 2, provided with a detectable label.

4. A diagnostic agent as claimed in claim 3, in which the DNA is provided with the radio label $^{32}$p.

5. Recombinant DNA containing vector DNA and an insertion therein of DNA of claim 1, having at least 60% homology relative to a portion of δ-RNA and being capable of selective hybridization with δ-RNA.

6. Recombinant DNA as claimed in claim 5, containing copy DNA of a portion of the δ-RNA, said copy DNA being capable of selective hybridization with δ-RNA.

7. A DNA selected from the group consisting of DNA having the following base sequence $5' \rightarrow$

| 10 | 20 | 30 |
|---|---|---|
| CCCCGTTGCT | TTCTTTACTT | TCCTCCTCGC |
| GGGGCAACGA | AAGAAATGAA | AGGAGGAGCG |
| 40 | 50 | 60 |
| TTCGGTCTCC | CCCTACTCCT | AGCATCTCCT |
| AAGCCAGAGG | GGGATGAGGA | TCGTAGAGGA |
| 70 | 80 | 90 |
| CCTATCGCTA | TGGTCTTACT | CCTACCGCTC |
| GGATAGCGAT | ACCAGAATGA | GGATGGCGAG |
| 100 | 110 | 120 |
| GAAGCGCCTC | TTGTTCGCTG | AAGGGGTCCT |
| CTTCGCGGAG | AACAAGCGAC | TTCCCCAGGA |
| 130 | 140 | 150 |
| CTGGAGGTGA | TTTCTCTGCT | CATCTCCGAG |
| GACCTCCACT | AAAGAGACGA | GTAGAGGCTC |
| 160 | 170 | 180 |
| TGGATTCCTC | CCTCTGGGTG | CTACTCAACC |
| ACCTAAGGAG | GGAGACCCAC | GATGAGTTGG |
| 190 | 200 | 210 |
| CTTCGGGCCG | GAGTGCTCTC | CAGATCTGGA |
| GAAGCCCGGC | CTCACGAGAG | GTCTAGACCT |
| 220 | 230 | 240 |
| GGTTGGGCCC | CTCGGATCGG | GAGGCCCGCT |
| CCAACCCGGG | GAGCCTAGCC | CTCCGGGCGA |
| 250 | 260 | 270 |
| CCTTTTTCTT | CCACCTTCCT | CTTTCCCCTT |
| GGAAAAAGAA | GGTGGAAGGA | GAAAGGGGAA |
| 280 | 290 | 300 |
| CCAGAGATTC | TCCGGCGTTG | TGGGGATCTC |
| GGTCTCTAAG | AGGCCGCAAC | ACCCCTATAG |
| 310 | 320 | 330 |
| GTCCGCTTCC | TGAGACCTCT | CTTTGCTTCT |
| CAGGCGAAGG | ACTCTGGAGA | GAAACGAAGA |
| 340 | 350 | 360 |
| TGGGAGTAGT | TTCTCCGACG | TTCCAATGCT |
| ACCCTCATCA | AAGAGGCTGC | AAGGTTACGA |
| 370 | 380 | 390 |
| CTTTACCGTG | ACATCCCCTC | TCGGGAGCTG |
| GAAATGGCAC | TGTAGGGGAG | AGCCCTCGAC |
| A | | |
| T ← 5', | | | a DNA homologous therewith as to at least 60%, or a portion thereof, and capable of selective hybridization with δ-RNA.

8. The DNA as claimed in claim 2, selected from the group consisting of DNA having the following base sequence $5' \rightarrow$

| 10 | 20 | 30 |
|---|---|---|
| CCCCGTTGCT | TTCTTTACTT | TCCTCCTCGC |
| GGGGCAACGA | AAGAAATGAA | AGGAGGAGCG |
| 40 | 50 | 60 |
| TTCGGTCTCC | CCCTACTCCT | AGCATCTCCT |
| AAGCCAGAGG | GGGATGAGGA | TCGTAGAGGA |
| 70 | 80 | 90 |
| CCTATCGCTA | TGGTCTTACT | CCTACCGCTC |
| GGATAGCGAT | ACCAGAATGA | GGATGGCGAG |

| | | |
|---|---|---|
| 100 | 110 | 120 |
| GAAGCGCCTC | TTGTTCGCTG | AAGGGGTCCT |
| CTTCGCGGAG | AACAAGCGAC | TTCCCCAGGA |
| 130 | 140 | 150 |
| CTGGAGGTGA | TTTCTCTGCT | CATCTCCGAG |
| GACCTCCACT | AAAGAGACGA | GTAGAGGCTC |
| 160 | 170 | 180 |
| TGGATTCCTC | CCTCTGGGTG | CTACTCAACC |
| ACCTAAGGAG | GGAGACCCAC | GATGAGTTGG |
| 190 | 200 | 210 |
| CTTCGGGCCG | GAGTGCTCTC | CAGATCTGGA |
| GAAGCCCGGC | CTCACGAGAG | GTCTAGACCT |
| 220 | 230 | 240 |
| GGTTGGGCCC | CTCGGATCGG | GAGGCCCGCT |
| CCAACCCGGG | GAGCCTAGCC | CTCCGGGCGA |
| 250 | 260 | 270 |
| CCTTTTTCTT | CCACCTTCCT | CTTTCCCCTT |
| GGAAAAAGAA | GGTGGAAGGA | GAAAGGGGAA |
| 280 | 290 | 300 |
| CCAGAGATTC | TCCGGCGTTG | TGGGGATCTC |
| GGTCTCTAAG | AGGCCGCAAC | ACCCCTATAG |
| 310 | 320 | 330 |
| GTCCGCTTCC | TGAGACCTCT. | CTTTGCTTCT |
| CAGGCGAAGG | ACTCTGGAGA | GAAACGAAGA |
| 340 | 350 | 360 |
| TGGGAGTAGT | TTCTCCGACG | TTCCAATGCT |
| ACCCTCATCA | AAGAGGCTGC | AAGGTTACGA |
| 370 | 380 | 390 |
| CTTTACCGTG | ACATCCCTC | TCGGGAGCTG |
| GAAATGGCAC | TGTAGGGAG | AGCCCTCGAC |
| | | A |
| | | T ← 5′, | a DNA homologous therewith as to at least 60%, or a portion thereof, and capable of selective hybridization with δ-RNA.

9. Recombinant DNA selected from the group consisting of DNA having the following base sequence

5′ →

| 10 | 20 | 30 |
|---|---|---|
| CCCCGTTGCT | TTCTTTACTT | TCCTCCTCGC |
| GGGGCAACGA | AAGAAATGAA | AGGAGGAGCG |
| 40 | 50 | 60 |
| TTCGGTCTCC | CCCTACTCCT | AGCATCTCCT |
| AAGCCAGAGG | GGGATGAGGA | TCGTAGAGGA |
| 70 | 80 | 90 |
| CCTATCGCTA | TGGTCTTACT | CCTACCGCTC |
| GGATAGCGAT | ACCAGAATGA | GGATGGCGAG |
| 100 | 110 | 120 |
| GAAGCGCCTC | TTGTTCGCTG | AAGGGGTCCT |
| CTTCGCGGAG | AACAAGCGAC | TTCCCCAGGA |
| 130 | 140 | 150 |
| CTGGAGGTGA | TTTCTCTGCT | CATCTCCGAG |
| GACCTCCACT | AAAGAGACGA | GTAGAGGCTC |
| 160 | 170 | 180 |
| TGGATTCCTC | CCTCTGGGTG | CTACTCAACC |
| ACCTAAGGAG | GGAGACCCAC | GATGAGTTGG |
| 190 | 200 | 210 |
| CTTCGGGCCG | GAGTGCTCTC | CAGATCTGGA |
| GAAGCCCGGC | CTCACGAGAG | GTCTAGACCT |
| 220 | 230 | 240 |
| GGTTGGGCCC | CTCGGATCGG | GAGGCCCGCT |
| CCAACCCGGG | GAGCCTAGCC | CTCCGGGCGA |
| 250 | 260 | 270 |
| CCTTTTTCTT | CCACCTTCCT | CTTTCCCCTT |
| GGAAAAAGAA | GGTGGAAGGA | GAAAGGGGAA |
| 280 | 290 | 300 |
| CCAGAGATTC | TCCGGCGTTG | TGGGGATCTC |
| GGTCTCTAAG | AGGCCGCAAC | ACCCCTATAG |
| 310 | 320 | 330 |
| GTCCGCTTCC | TGAGACCTCT | CTTTGCTTCT |
| CAGGCGAAGG | ACTCTGGAGA | GAAACGAAGA |
| 340 | 350 | 360 |
| TGGGAGTAGT | TTCTCCGACG | TTCCAATGCT |
| ACCCTCATCA | AAGAGGCTGC | AAGGTTACGA |
| 370 | 380 | 390 |
| CTTTACCGTG | ACATCCCCTC | TCGGGAGCTG |
| GAAATGGCAC | TGTAGGGAG | AGCCCTCGAC |
| | | A |
| | | T ← 5′, | a DNA homologous therewith as to at least 60%, or a portion thereof, and capable of selective hybridization with δ-RNA.

\* \* \* \* \*

UNITED STATES PATENT AND TRADEMARK OFFICE
CERTIFICATE OF CORRECTION

PATENT NO. : 4,959,462
DATED : September 25, 1990
INVENTOR(S) : DIJKEMA ET AL

It is certified that error appears in the above-indentified patent and that said Letters Patent is hereby corrected as shown below:

On the title page: Item [56] Foreign Application

Priority Data", delete "Jul. 31, 1984 [NL] Netherlands 8402392" under "Foreign Application.

Column 5,

Claim 1, line 1: after "The DNA" insert -- of Claim 7--.

Claim 3, line 2: delete "Claims 1 and 2" and insert therefor --Claims 1, 2 and 7--.
Column 6,
Claim 7, line 1: after "A DNA" insert --,--.

Signed and Sealed this

Twenty-eighth Day of December, 1993

Attest:

BRUCE LEHMAN

Attesting Officer    Commissioner of Patents and Trademarks